United States Patent [19]

Daugherty

[11] Patent Number: 5,462,533
[45] Date of Patent: Oct. 31, 1995

[54] SELF CONTAINED NEEDLE AND SHIELD

[75] Inventor: Charles W. Daugherty, Sandy, Utah

[73] Assignee: Becton, Dickinson and Company, Franklin Lakes, N.J.

[21] Appl. No.: 370,331

[22] Filed: Jan. 9, 1995

Related U.S. Application Data

[63] Continuation of Ser. No. 96,794, Jul. 23, 1993, abandoned.

[51] Int. Cl.⁶ .................................................. A61M 5/178
[52] U.S. Cl. ........................ 604/164; 604/264; 604/198
[58] Field of Search .................................. 604/164, 165, 604/168, 198, 263, 264, 272

[56] References Cited

U.S. PATENT DOCUMENTS

| | | | |
|---|---|---|---|
| Re. 34,223 | 4/1993 | Bonaldo | 604/164 |
| 2,711,732 | 6/1955 | Solomon | 128/215 |
| 2,876,770 | 3/1959 | White | 128/215 |
| 3,134,380 | 5/1964 | Armao | 128/215 |
| 3,354,881 | 11/1967 | Bloch | 128/215 |
| 3,401,693 | 9/1968 | Cohen | 128/221 |
| 3,536,073 | 10/1970 | Farb | 128/214.4 |
| 3,884,230 | 5/1975 | Wulff | 128/221 |
| 4,139,009 | 2/1979 | Alvarez | 128/218 |
| 4,160,450 | 7/1979 | Doherty | 128/214.4 |
| 4,170,993 | 10/1979 | Alvarez | 128/214 |
| 4,660,570 | 4/1987 | Dombrowski | 128/765 |
| 4,735,618 | 4/1988 | Hagen | 604/192 |
| 4,747,831 | 5/1988 | Kulli | 604/110 |
| 4,762,516 | 8/1988 | Luther et al. | 604/164 |
| 4,778,453 | 10/1988 | Lopez | 604/110 |
| 4,781,692 | 11/1988 | Jagger et al. | 604/164 |
| 4,832,696 | 5/1989 | Luther et al. | 604/164 |
| 4,834,718 | 5/1989 | McDonald | 604/195 |
| 4,846,805 | 7/1989 | Sitar | 604/165 |
| 4,846,809 | 7/1989 | Sims | 604/198 |
| 4,846,811 | 7/1989 | Nanderhoof | 604/263 |
| 4,850,961 | 7/1989 | Wanderer et al. | 604/53 |
| 4,906,236 | 3/1990 | Alberts et al. | 604/198 |
| 4,911,694 | 3/1990 | Dolan | 604/198 |
| 4,917,669 | 4/1990 | Bonaldo | 604/164 |
| 4,929,241 | 5/1990 | Kulli | 604/263 |
| 4,935,012 | 6/1990 | Magre et al. | 604/192 |
| 4,950,252 | 8/1990 | Luther et al. | 604/164 |
| 4,952,207 | 8/1990 | Lemieux | 604/164 |
| 4,955,866 | 9/1990 | Corey | 604/192 |
| 5,013,304 | 5/1991 | Russell et al. | 604/164 |
| 5,019,049 | 5/1991 | Haining | 604/165 |
| 5,049,136 | 9/1991 | Johnson | 604/198 |
| 5,102,394 | 5/1992 | Lasaitis | 604/164 |
| 5,116,323 | 5/1992 | Kreuzer et al. | 604/164 |
| 5,120,317 | 6/1992 | Luther | 604/158 |
| 5,171,231 | 12/1992 | Heiliger | 604/164 |

FOREIGN PATENT DOCUMENTS

WO88/07388 10/1988 WIPO .

*Primary Examiner*—John G. Weiss
*Attorney, Agent, or Firm*—Eric M. Lee

[57] ABSTRACT

A surgical needle is disclosed which is made up of two concentric tubes. The inner tube has a sharp tip like a conventional hypodermic or intravenous needle. The inner tube can be retracted into the outer tube after use. In one embodiment, the needle forms part of a catheter assembly. A catheter is mounted coaxially around the both tubes. The inner tube has a latching member attached to the end without the sharp tip. The latching member engages detents on a housing to hold the sharp tip in an extended position or a retracted position. The latching member is provided with a porous plug to assist in venting gases during catheter introduction.

7 Claims, 4 Drawing Sheets

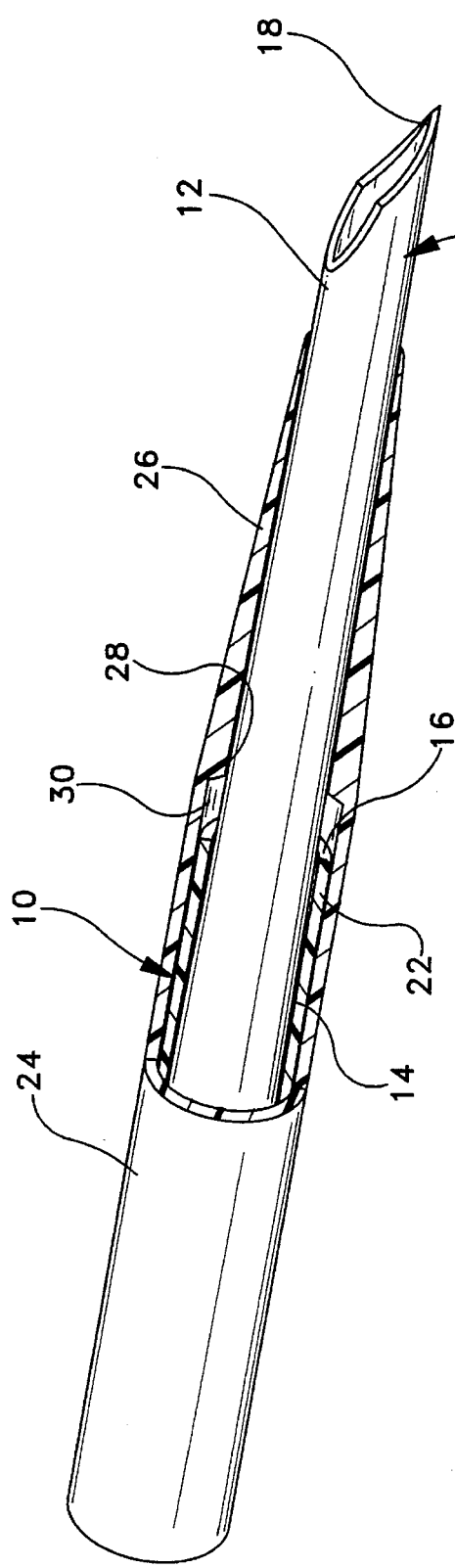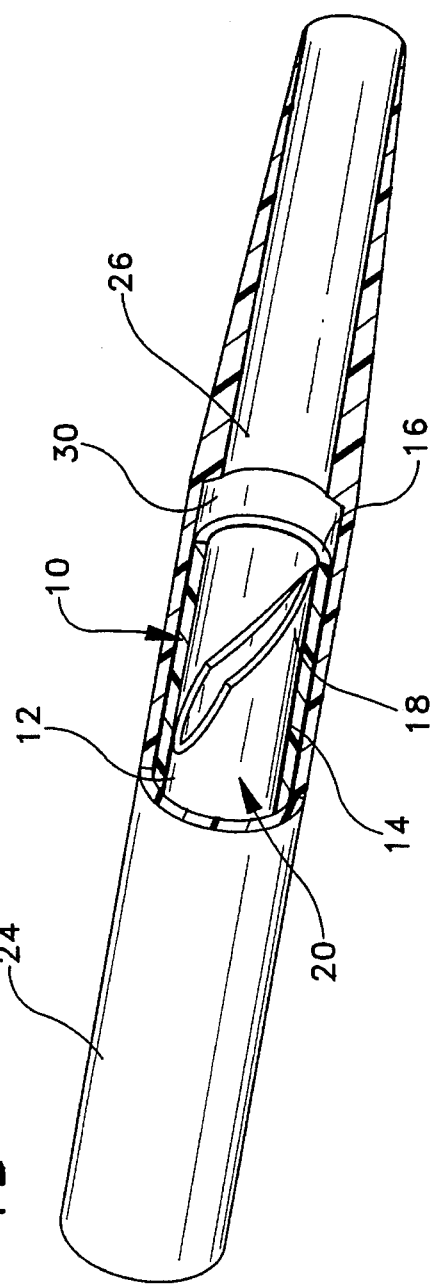

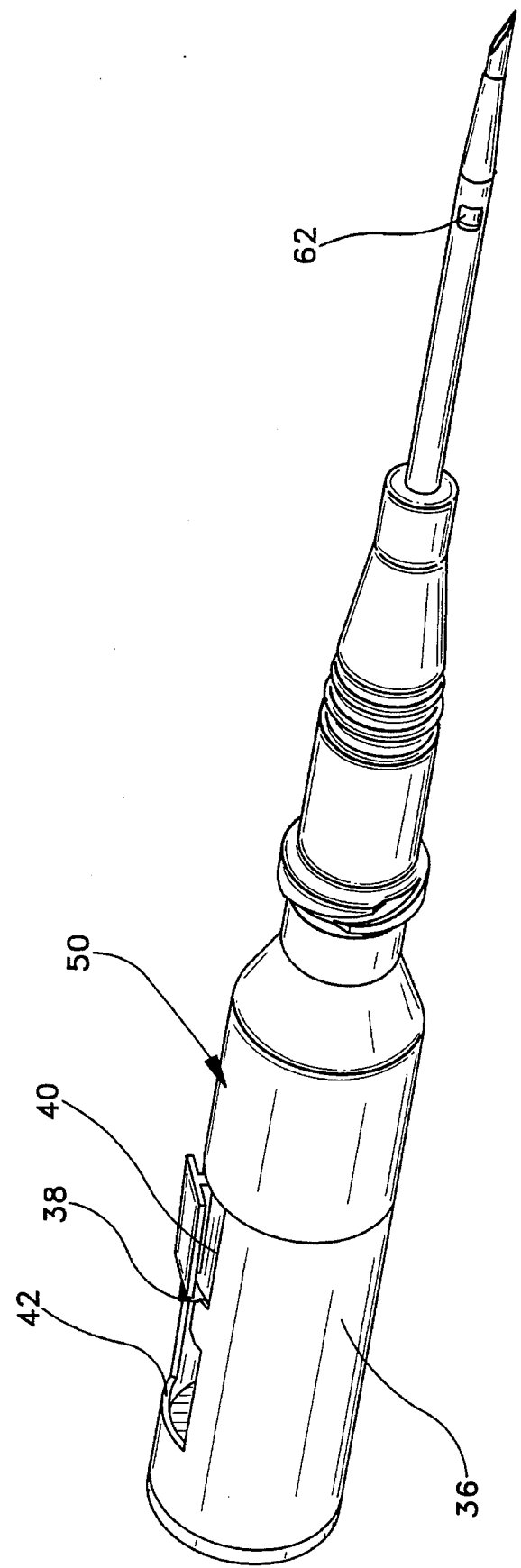

SELF CONTAINED NEEDLE AND SHIELD

This application is a continuation of application Ser. No. 08/096,794, filed on Jul. 23, 1993 and is now abandoned.

BACKGROUND

This invention relates to surgical needles. More specifically, it relates to a catheter introduction device equipped with a needle shielding feature to shield the needle after withdrawal of the needle from the blood vessel.

With the proliferation of the AIDS virus, attention has increasingly focused on the transmission of blood borne pathogens from infected to healthy people. The transmission of blood borne pathogens through needle-stick injuries has received special attention.

Several devices have been proposed for the shielding of surgical needles after use. For catheter introducer needles, such shields have been in the form of sheaths which attach to the needle hub (e.g. McDonald's U.S. Pat. No. 4,834,718, Luther et al.'s U.S. Pat. No. 4,762,516) and sheaths which attach to a stop on the needle (e.g. Lopez's U.S. Pat. No. 4,778,453, Vanderhoof's U.S. Pat. No. 4,846,811). These devices prevent the sheath from sliding off the end of the needle by restraining the rear of the sheath. Other device include a barrier which prevents the sheath from being pulled back to expose the needle tip (e.g. Kulli's U.S. Pat. No. 4,929,241). In the cited references, a conventional needle is shielded by a separate sliding sheath. In contrast, the present invention focuses on the design of the needle and involves a redesigned needle which incorporates a sheath.

SUMMARY OF THE INVENTION

The invention is a surgical needle having two coaxial tubes. One tube is fixed to a housing and the other is slidable relative to the housing. The inner tube has a sharp tip. When the needle is used to penetrate the body, the sharp tip protrudes from the outer tube and the inner tube is held in place by a latch. Once the needle has been used, the inner tube is withdrawn into the outer tube and latched into a shielded position. The sharp tip is thus shielded by the outer tube.

BRIEF DESCRIPTION OF THE DRAWINGS

FIG. 1A is a partially cut away view of the needle of the present invention in a first position in which the sharp tip of the needle protrudes from the outer tube;

FIG. 1B is a partially cut away view of the needle of the present invention in which the sharp tip of the needle is shielded by the outer tube;

FIG. 2 is a perspective view of an embodiment of the invention in which the needle forms part of a catheter introducer assembly;

DETAILED DESCRIPTION OF THE DRAWINGS

Figure 3:
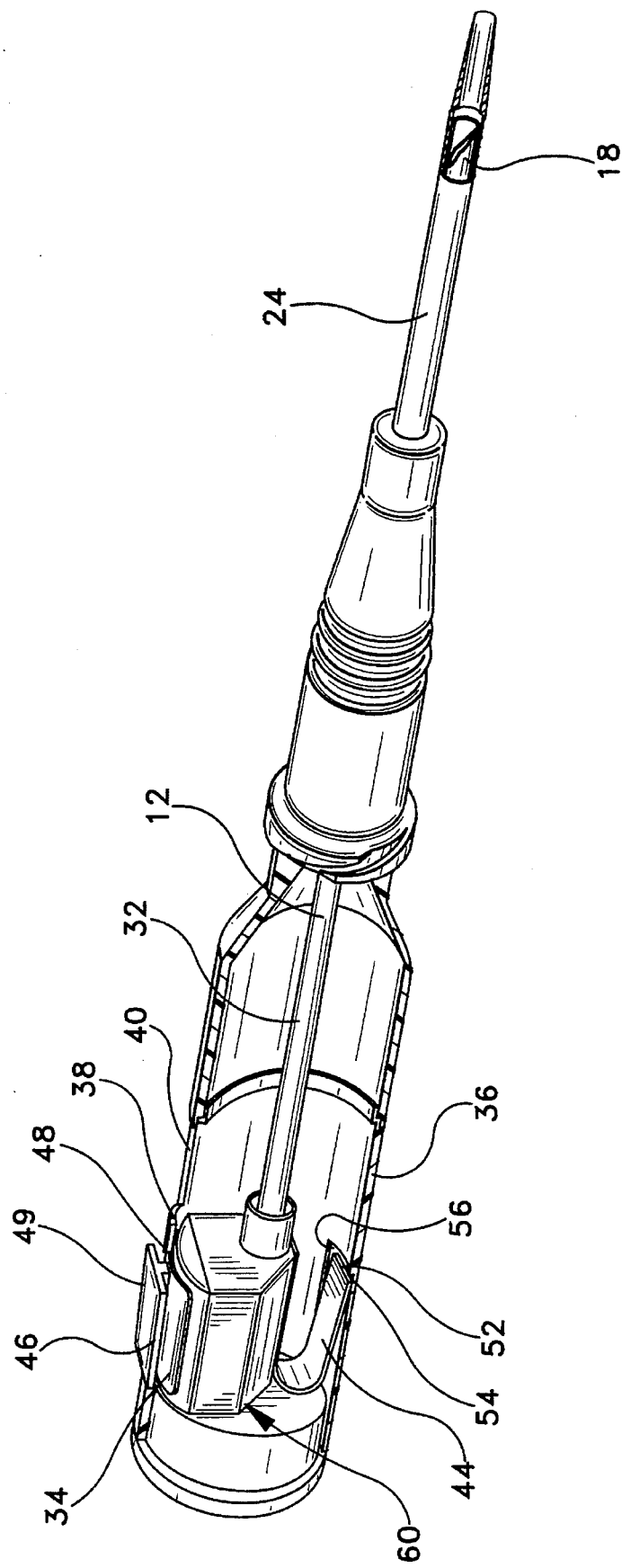
FIG. 3 is a partially cut away perspective view of the embodiment of FIG. 2.

The distal end of needle 10 is shown in FIG. 1A. Needle 10 is made up of first tube 12 and second tube 14. Second tube 14 is mounted coaxially around first tube 12. Between first and second tubes 12 and 14 is annular space 16. First tube 12 is a needle having sharp point 18 at its distal end 20. In a first position shown in FIG. 1A, sharp tip 18 protrudes from distal end 22 of second tube 14.

In the embodiment illustrated fully in FIG. 1A, surrounding first and second tubes 12 and 14 is catheter 24 which has an inner lumen 30. Inner lumen 30 is dimensioned to accommodate first tube 12 in its distal end 26 and second tube 14 in main body 28. Catheter 24 thus has an exaggerated step in its inner lumen 30.

In FIG. 1B, first tube 12 is shown retracted into second tube 14. The stepped configuration of catheter 24 is more clearly shown in FIG. 1B.

Needle Hub 50 is shown in perspective view in FIG. 2 and in partially cut away perspective view in FIG. 3. Attached to proximal end 32 of first tube 12 is latching member 34 for moving second tube 14 relative to first tube 12. Housing 36 is provided with cutouts which form guide 38 and second and first detents 40 and 42. Web 48 is secured to raised portion 49 which is dimensioned to fit into and close detents 40 and 42. Latching member 34 is also provided with web 48 which is designed to slide along guide 38 from first detent 40 to second detent 42. Latching member 34 is also provided with leaf spring 44 which is biased so that when latching member 34 is in first detent 40 (i.e. first tube is in a first position in which sharp tip 18 protrudes from second tube), spring 44 tends to hold latching member in first detent 40.

Latching member 34 is provided with thumb plate 46 which is attached to web 48. When pressure is applied to thumb plate 46, latching member 34 can be disengaged from first detent 40 (i.e. when raised portion 49 is pushed down and out of first detent 40) and moved towards second detent 42 so that first tube 12 is in a second position in which sharp tip 18 is shielded by second tube 14. Housing 36 is provided with further detent 52, in the form of an indentation in housing 36. When latching member 34 reaches second detent 42, end portion 54 of spring 44 engages step 56 of the indentation. The bias of spring 44 forces raised portion 49 of latching member 34 into second detent 42. The engagement of spring end portion 54 with step 56 prevents latching member 34 from moving back to first detent 40, thereby ensuring that sharp tip 18 remains shielded by second tube 14.

Figure 4:
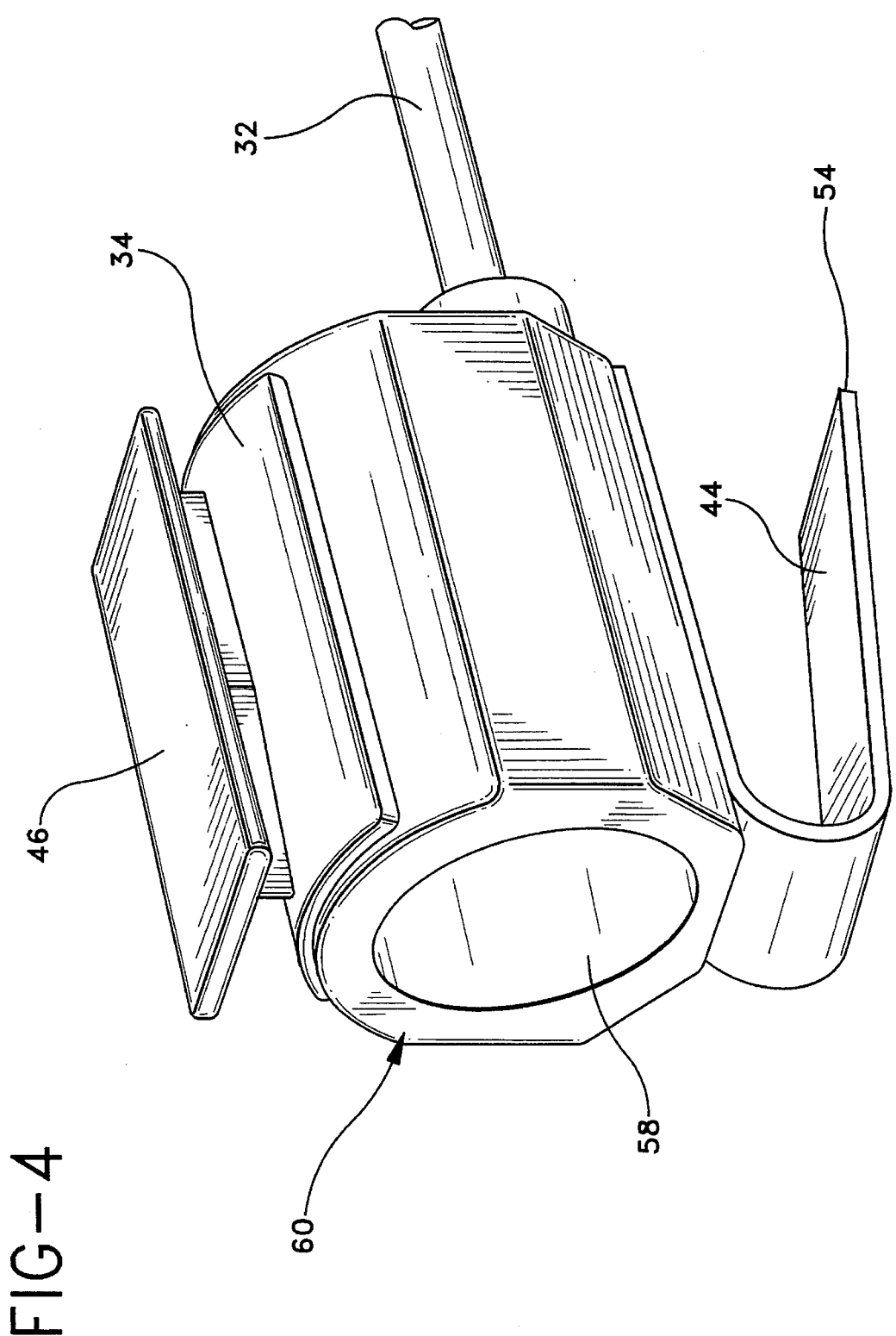
FIG. 4 is a perspective view of the latch member of the invention showing a flash back plug.

The invention is inserted in the same way as a typical over the needle catheter introducer, for example the Insyte® catheter available from Becton, Dickinson and Company, Sandy, Utah. When distal end 20 of first tube 12 enters a blood vessel, blood will flow up the inner lumen of first tube 12. The presence of this blood is useful in determining whether a vessel, as opposed to tissue has been penetrated. For this reason, latching member 34 is provided with hollow flashback chamber 58 (FIG. 4) through which blood can flow from the lumen of first tube 12. Latch member 34 is also provided with porous flash back plug 60 through which gases may be vented. Housing 36 and latching member 34 are translucent to allow flashback to be observed.

In order to use the invention with a standard catheter, first tube 12 must be slightly smaller in diameter than a conventional catheter introducer needle. For a snug fit between catheter 26 and first tube 12 at a distal end 20, the minor lumen of catheter 26 must be narrow. For this reason, hole 62 is provided in catheter 24 to provide increased fluid flow through catheter 24.

The invention is made using molding and needle manufacturing techniques well known to those of ordinary skill in the art.

The foregoing describes a preferred embodiment of the invention. It is intended to be illustrative rather than limiting. The full scope of the invention is to be determined by

I claim:

1. A surgical needle assembly, comprising:

a hollow housing having a proximal end and a distal end and defining a slot therein, the slot having a medial portion, a distal portion and a proximal portion wherein the medial portion has a width that is less than the width of the distal portion and the proximal portion;

a hub movably disposed in the housing, the hub having a raised latching portion adapted to engage the distal portion of the slot when the hub is distal of the proximal end of the housing and to engage the proximal portion of the slot when the hub is adjacent the proximal end of the housing so as to axially lock the hub with respect to the housing;

a needle with a sharp distal tip and a proximal end affixed to the hub; and a spring connected to the hub to bias the hub toward the slot.

2. The surgical needle assembly of claim 1 wherein the spring is a leaf spring having an elongated portion in contact with an inner surface of the housing.

3. The surgical needle assembly of claim 2 wherein the inner surface of the housing defines a cut out portion to engage the elongated portion of the leaf spring and to prevent movement of the leaf spring toward the distal end of the housing when the raised latching portion of the hub is engaged with the proximal portion of the slot.

4. The surgical needle assembly of claim 1 further comprising a tube with a distal end and a proximal end connected to the distal end of the housing with the needle being disposed in the tube so that the sharp distal tip of the needle extends beyond the distal end of the tube when the raised latching portion of the hub is engaged with the distal portion of the slot and the sharp distal tip of the needle is proximal of the distal end of the tube when the raised latching portion of the hub is engaged with the proximal portion of the slot.

5. The surgical needle assembly of claim 4 further comprising a catheter cannula mounted coaxially around the tube.

6. The surgical needle assembly of claim 5 wherein the spring is a leaf spring having an elongated portion in contact with an inner surface of the housing.

7. The surgical needle assembly of claim 6 wherein the inner surface of the housing defines a cut-out portion to engage the elongated portion of the leaf spring and to prevent movement of the leaf spring toward the distal end of the housing when the raised latching portion of the hub is engaged with the proximal portion of the slot.

* * * * *